United States Patent
Abulhaj et al.

(10) Patent No.: US 6,852,119 B1
(45) Date of Patent: Feb. 8, 2005

(54) ADJUSTABLE DISPOSABLE LANCET AND METHOD

(76) Inventors: Ramzi F. Abulhaj, 18520 SW. 39th St., Miramar, FL (US) 33029; Erol Celikoglu, 20185 E. Country Club Dr., Apt. 2401, Aventura, FL (US) 33180; Yinggan Shi, 42 Xixin Road, Zhangjing Town, Wuxi City, CHI Jiangsu 214194 (CN)

( * ) Notice: Subject to any disclaimer, the term of this patent is extended or adjusted under 35 U.S.C. 154(b) by 0 days.

(21) Appl. No.: 10/237,370

(22) Filed: Sep. 9, 2002

(51) Int. Cl.[7] .............................................. A61B 17/32
(52) U.S. Cl. ....................................... 606/182; 606/172
(58) Field of Search ................................ 606/181, 182, 606/185

(56) References Cited

U.S. PATENT DOCUMENTS

| | | | | |
|---|---|---|---|---|
| 4,637,403 A | * | 1/1987 | Garcia et al. ................ 128/770 |
| 4,817,603 A | * | 4/1989 | Turner et al. ............ 128/329 R |
| RE32,922 E | | 5/1989 | Levin et al. |
| 5,026,388 A | | 6/1991 | Ingalz |
| 5,350,392 A | * | 9/1994 | Purcell et al. ............... 606/182 |
| 5,527,334 A | | 6/1996 | Kanner et al. |
| 5,613,978 A | | 3/1997 | Harding |
| 5,797,940 A | | 8/1998 | Mawhirt et al. |
| 5,833,660 A | * | 11/1998 | Nathan et al. ............... 604/110 |
| 5,871,494 A | * | 2/1999 | Simons et al. ............... 606/181 |
| 6,022,366 A | * | 2/2000 | Schraga ....................... 606/181 |
| 6,106,537 A | * | 8/2000 | Crossman et al. ........... 606/181 |
| 6,168,606 B1 | * | 1/2001 | Levin et al. ................. 606/181 |
| 6,210,420 B1 | * | 4/2001 | Mauze et al. ................ 606/182 |
| 6,258,112 B1 | | 7/2001 | Schraga |
| 6,322,574 B1 | * | 11/2001 | Lloyd et al. ................. 606/181 |
| 2001/0027327 A1 | * | 10/2001 | Schraga ....................... 606/182 |
| 2002/0087180 A1 | * | 7/2002 | Searle et al. ................. 606/181 |

* cited by examiner

*Primary Examiner*—David O. Reip
*Assistant Examiner*—Charles H. Sam

(57) ABSTRACT

The invention of the present disposable adjustable lancet involves an assembly which has a body and a cap. A lancet holder fits in the body and has a base portion having a pair of upstanding retainer-disabling tines, one of the tines is longer than the other to block the reinsertion of the lancet. A selector tip assists in engaging a clicker position in the selector tip. The method involves selecting positions by means of a female and a male position clicker which provide an audible signal. The position of the lancet can be determined in three manners: visually observing the degree of rotation, audibly denoting the click, and physically rotating the member which, in turn, results in a reaction on the finger while the adjustment is being made.

20 Claims, 7 Drawing Sheets

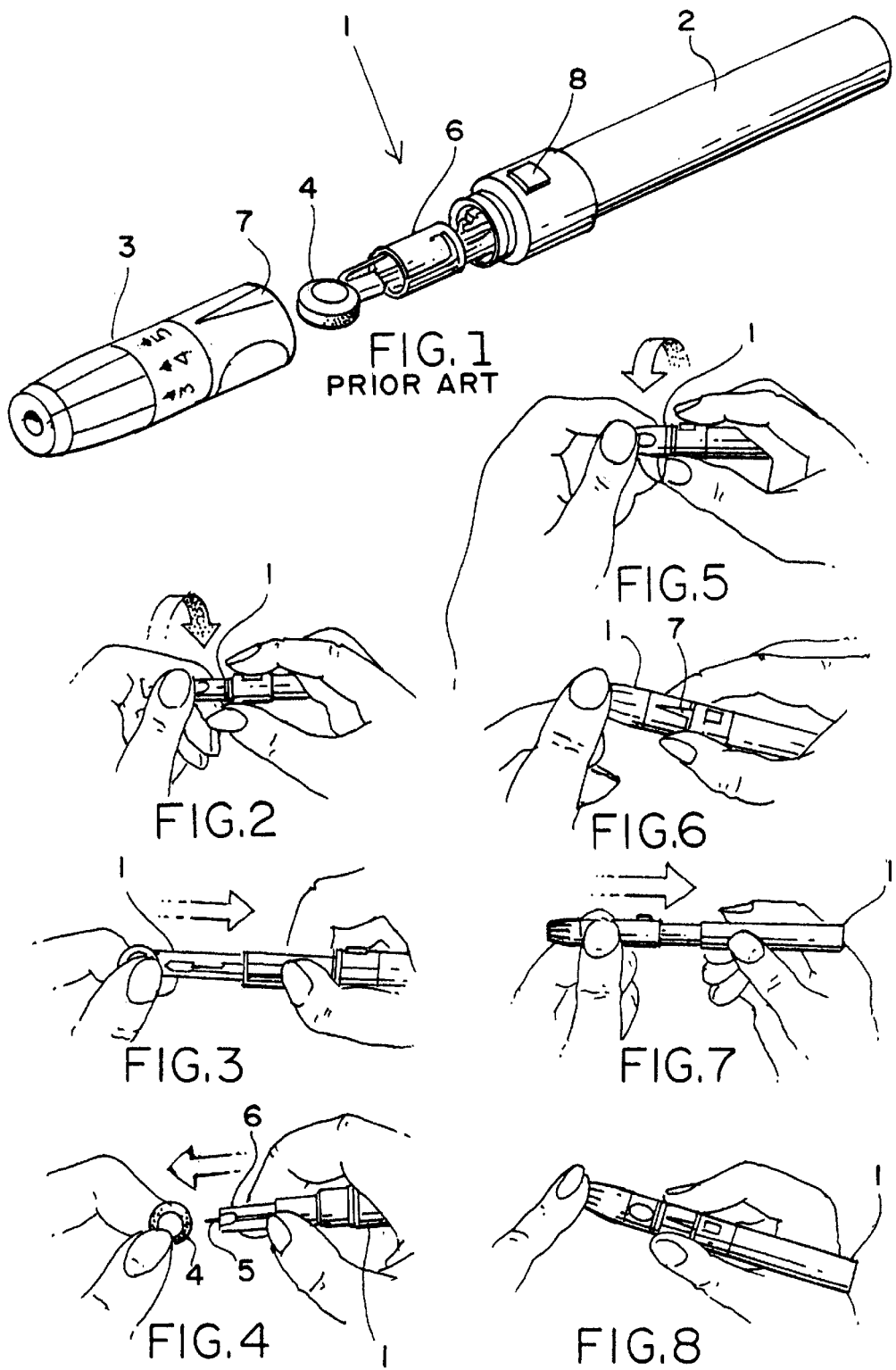

ADJUSTABLE DISPOSABLE LANCET AND METHOD

FIELD OF THE INVENTION

The present invention relates to lancets which are used to penetrate the skin in order to draw blood samples. Quite often they are used on a daily basis by diabetics. They are use on a regular basis on newborn infants.

BACKGROUND OF THE INVENTION

Lancing devices of various shapes and forms have been known in the art for years. Examples of such lancets are marketed as ProCare LLC. and also by Owen Mumford and Surgilance. Such lancets may be disposable, or they may require replacement of the lancet in a semi-permanent body portion.

Important to the operation of a lancet is developing a known depth of penetration into the skin which can be held within very minute tolerances. In many instances, it is important that lancets be disposable. There is a great need for disposable lancets which have an adjustable depth. In addition, such lancets require the utilization of a needle or a blade, depending upon the application. For example, blade type lancets are used with newborn infants and for pediatric purposes. The penetration is less painful, and to a depth not necessarily needed with the mature person and the mature skin.

SUMMARY OF THE INVENTION

The invention of the present disposable adjustable lancet involves an assembly which has a body and a cap. Ideally the two items are square in cross-sectional configuration. At one end of the body provision is made for a lancet holder. The lancet holder includes a lancet barrel portion, a follower for the adjustable support member, and a needle stop which ensures the extent of penetration of the needle.

The lancet also involves a cylindrical body portion used in combination with a coil spring. At the base of the unit is a lancet holder. The lancet holder has a base portion, and extending from the base portion are a pair of upstanding retainer-disabling tines, one of the tines being longer than the other. At the end of each tine, remote from the base, a pair of offset latches are provided to retain the lancet on the cocked position.

Finally, the selector tip is secured at the upper portion of the body and is provided with an internal helical cam segment or arc which engages a follower on the plunger unit. In addition, the selector tip utilizes a pair of opposed male detents which assist in engaging the female clicker position in the selector tip.

The method of the present invention involves the combining of members for an adjustable lancet in which provision is made for a minimum of two positions of depth. Three positions are considered optional considering size and the fact that two versions are offered. The multiple positions of depth are achieved through the interaction of a cam in the form of an interrupted helix segment or arc and the follower which moves the base member upwardly and downwardly. The selecting positions by means of a female and a male position clicker provide an audible signal so the position of the lancet can be determined in three manners: visually observing the degree of rotation, audibly denoting the click, and physically rotating the member to go to the various positions of the support which, in turn, results in a reaction on the finger while the adjustment is being made to determine the depth of penetration.

In view of the foregoing it is a principal object of the present invention to provide an adjustable multi-depth position, one use, disposable lancet.

Another object of the present invention is to provide an adjustable multi-depth position lancet with positive depth verification provided by a coordination between the extent of the penetration of the needle and a stop in the lancet body itself.

Yet another object of the present invention is to ensure that an audible click is generated in the moving of the lancet control to the different depth positions. While two or more depths are the subject of this invention, it is disclosed with three separate depths which are variated in accordance with accepted laboratory and medical standards.

Yet another object of the present invention is to provide the subject lancet with a finger sensitive position, a square body which resists slippage in adjustment, a round adjuster so that by feeling with both the body and the adjuster the depth setting can be differentiated without a visual reminder. The cap portion is provided in a square which can be positioned in any position, but will not position itself for purposes of recocking and recharging the lancet.

A significant objective of the invention is to be disposable, and that is achieved through a construction which blocks any reloading of the lancet after the lancet has been discharged from its original cocked position.

Finally, it is a major object of the present invention to be cost effectively competitive with pre-existing lancets which do not afford the advantages of adjustability, multiple depth positions, disposability, positive depth verification and audio-visual adjustable control.

DESCRIPTION OF ILLUSTRATIVE EMBODIMENTS

Further objects and advantages of the present invention will become apparent as the following description proceeds, taken in conjunction with the accompanying illustrative drawings in which:

FIG. 1 is a perspective opened view of a prior art lancing device;

FIG. 2 shows the prior art lancing device with the left hand twisting off the lance device cover;

Figure 9A:
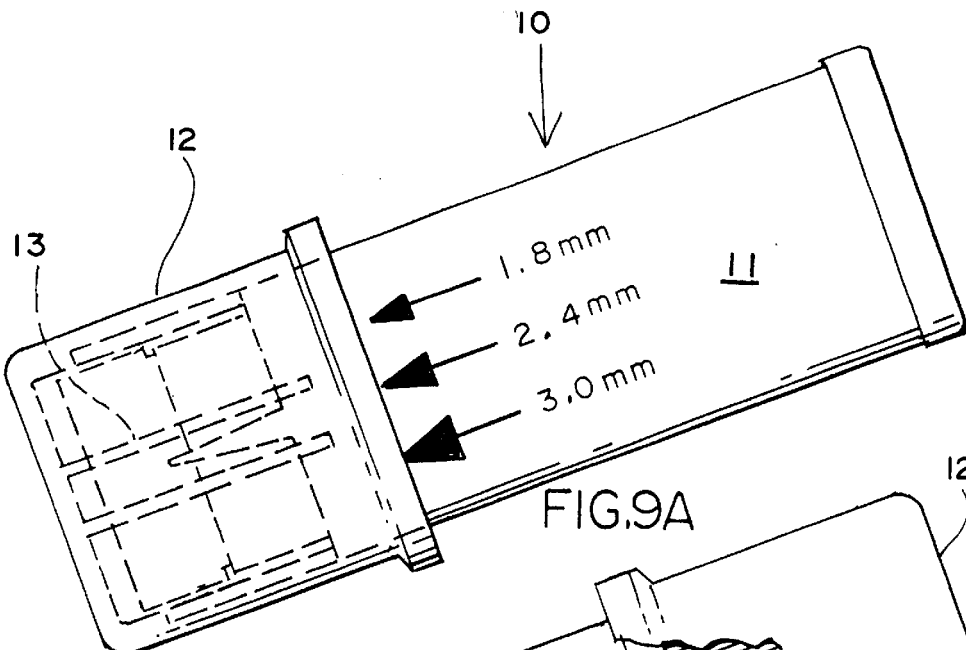
Figure 9B:
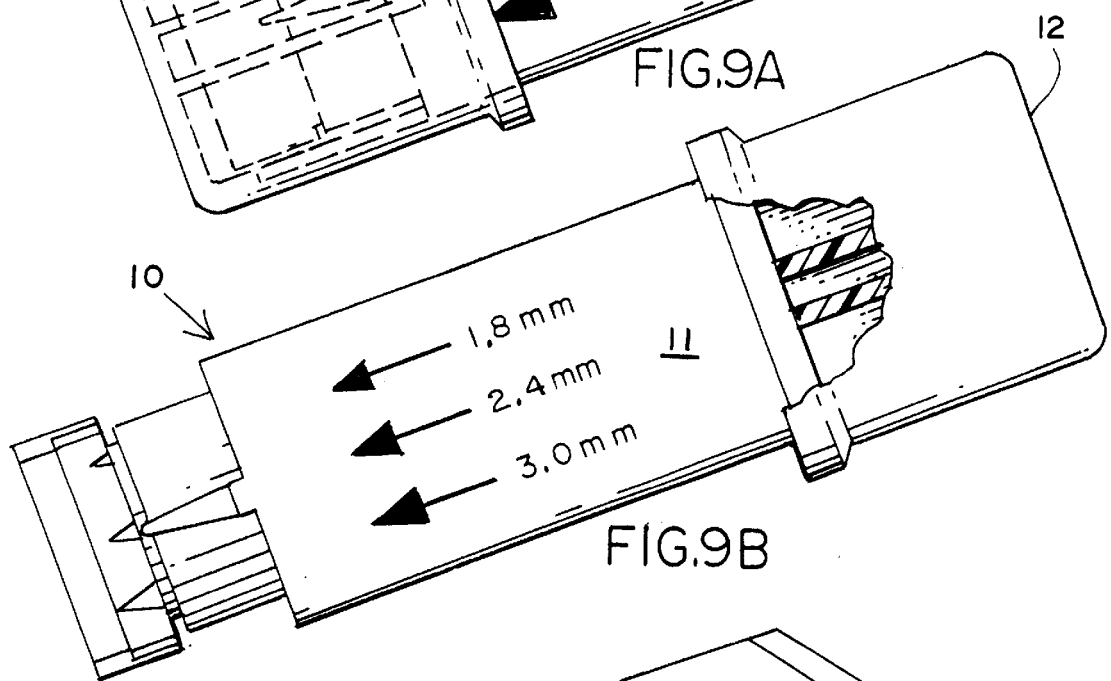
Figure 10:
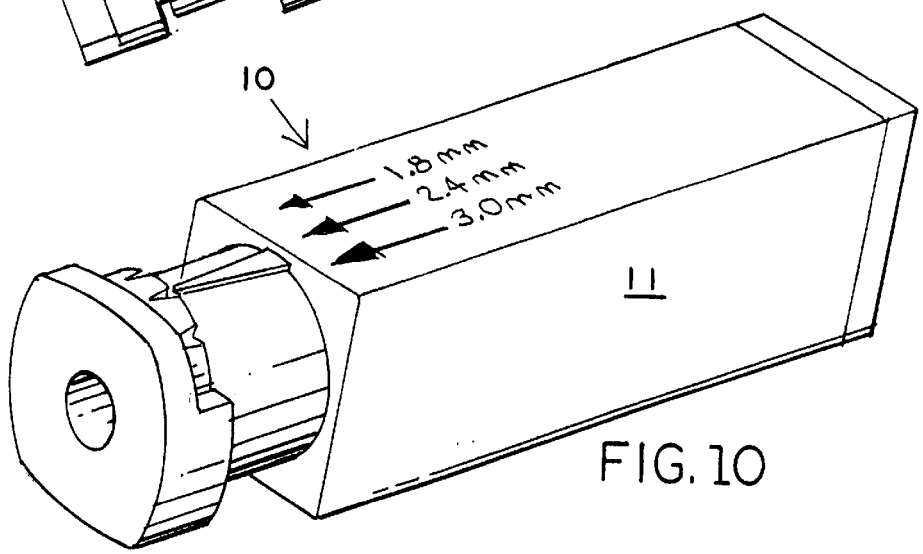
Figure 11:
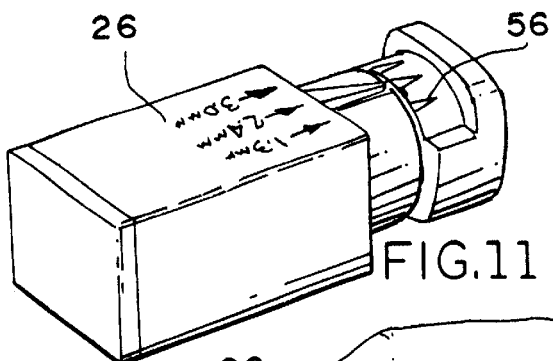
Figure 12:
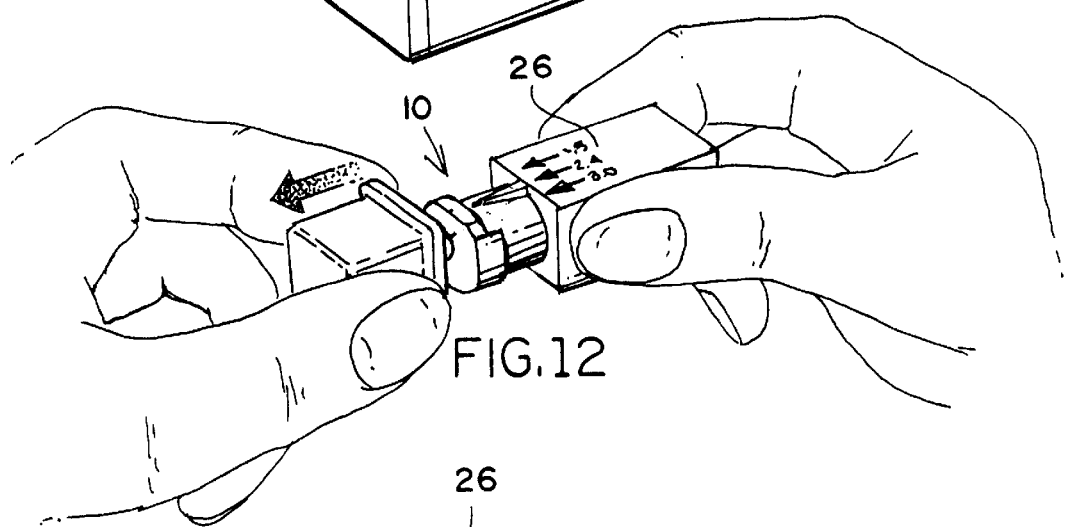
Figure 13:
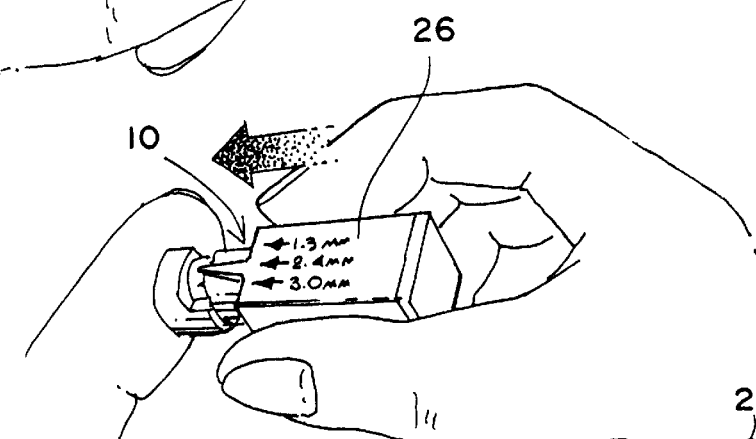
Figure 14:
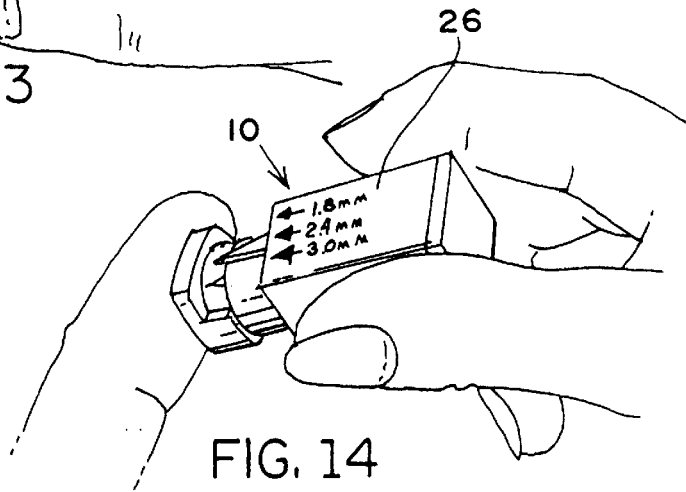
Figure 15:
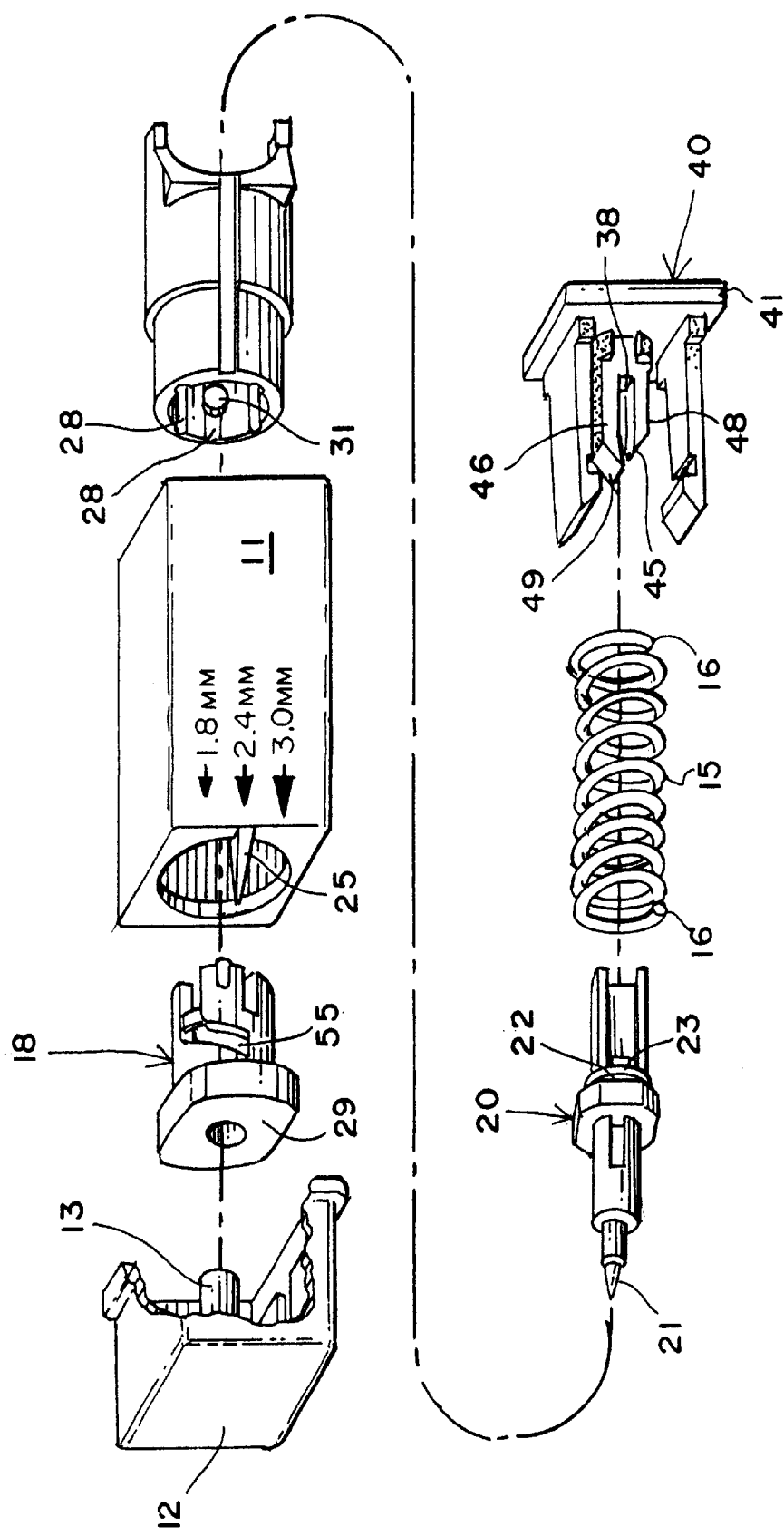
Figure 16:
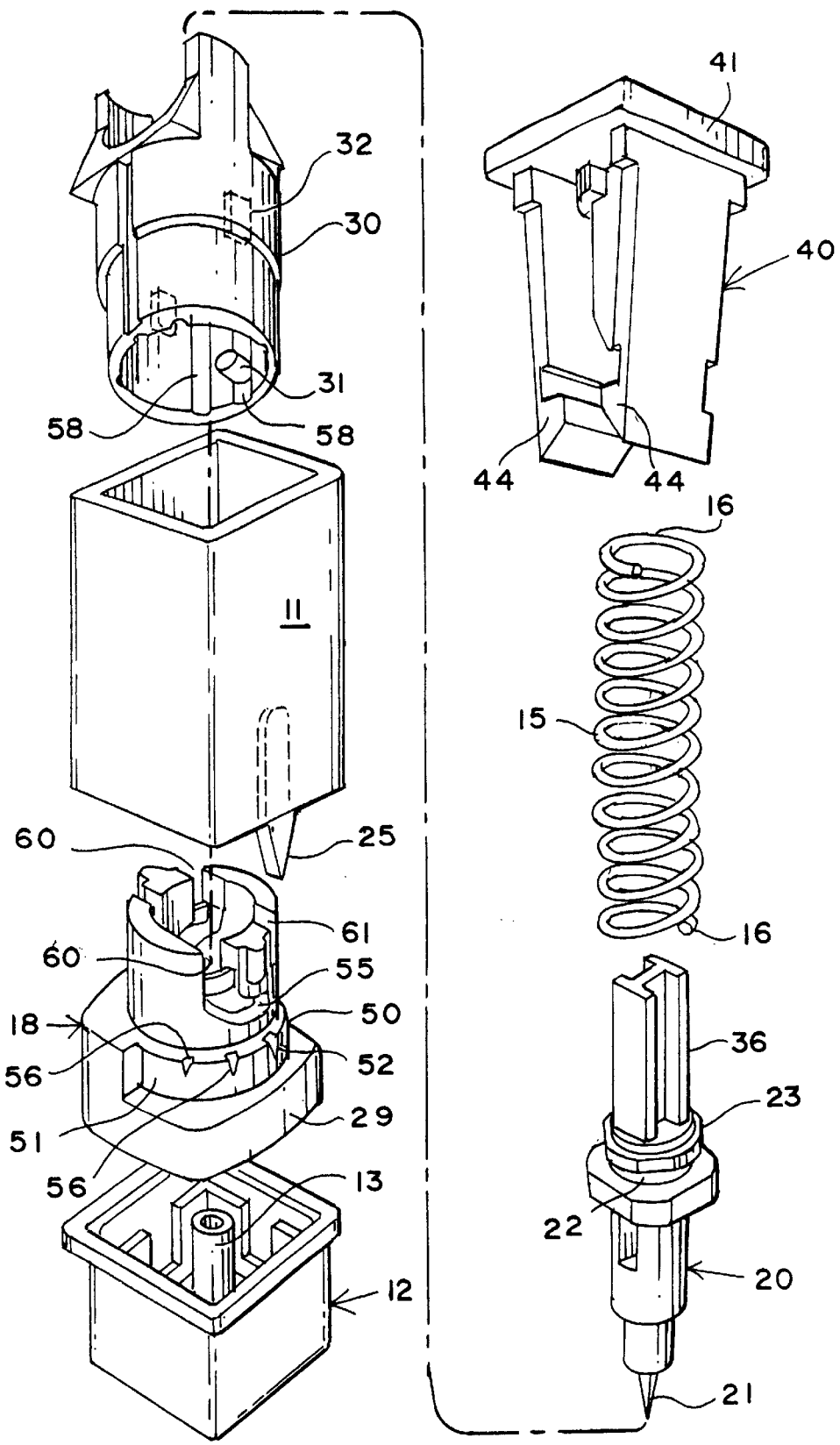
Figure 17:
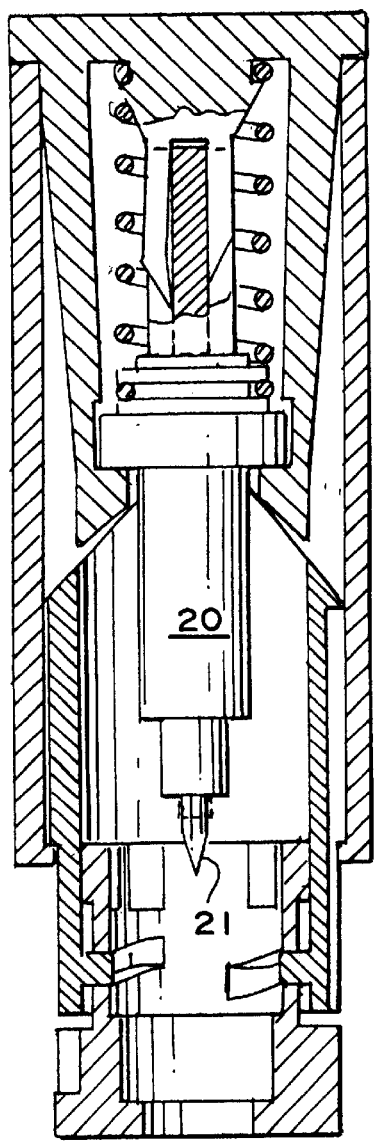
Figure 18:
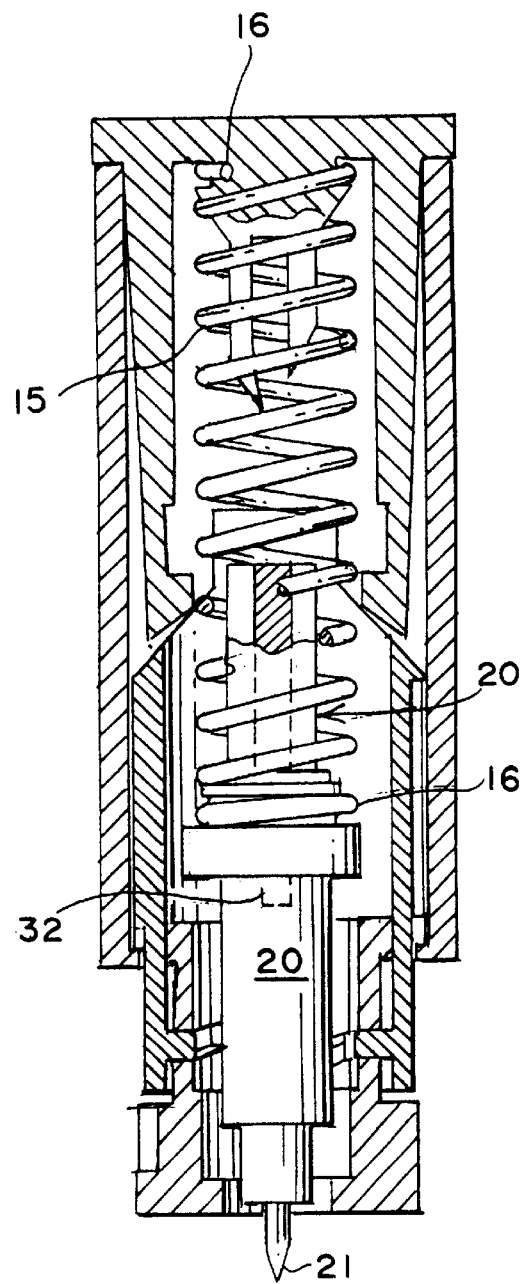
Figure 19:
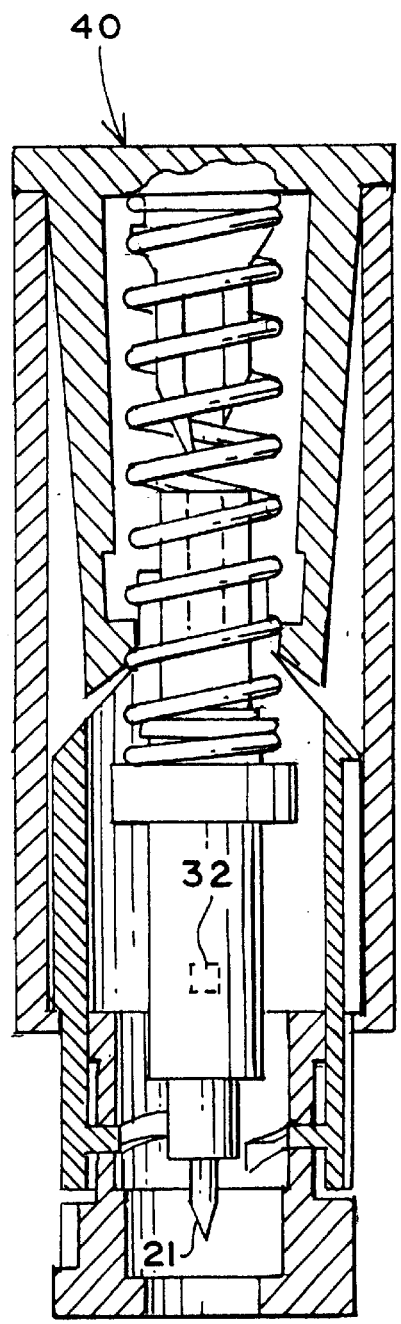
Figure 20:
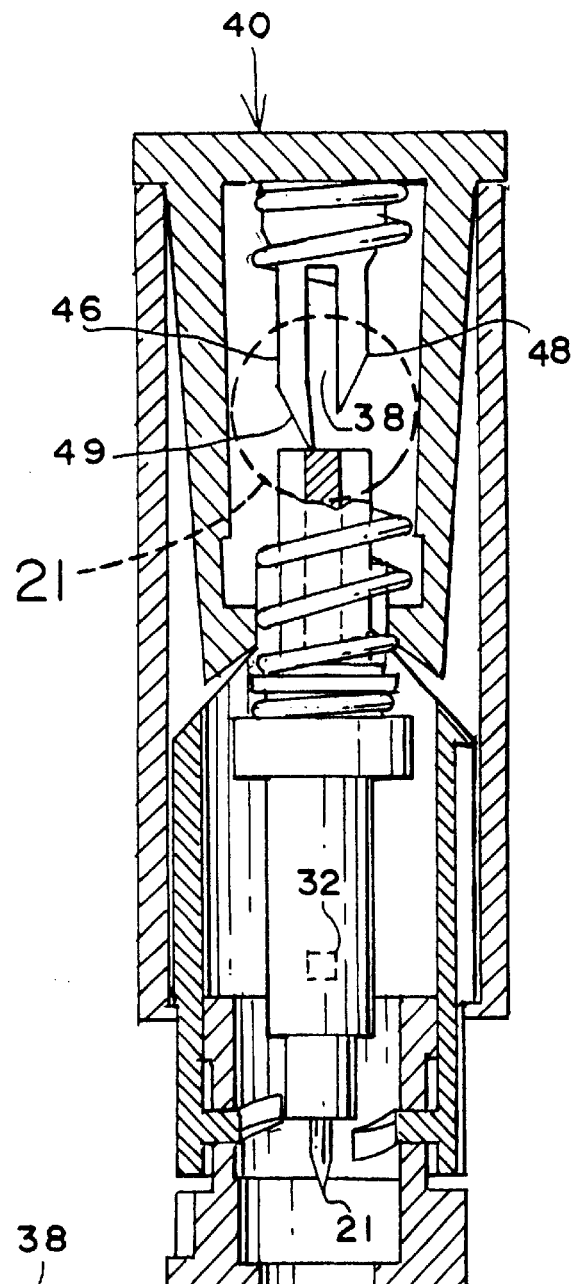

FIG. 3 discloses the insertion of the new lancet firmly into the lancet carrier;

FIG. 4 shows the left hand twisting off the lancet disk cover from the lancet;

FIG. 5 shows replacing the lancet cover;

FIG. 6 shows the left hand adjusting the comfort tip to one of the levels shown in the numerical indicia;

FIG. 7 shows the pulling of the lancet cover into the cocked position;

FIG. 8 shows the position of the adjustable comfort tip against the tip of the finger when the trigger button is then activated and the lancing completed;

FIGS. 9A and 9B are a composite view of the illustrative disposable adjustable lancet showing in front elevation the adjustment indicia in FIG. 9A and showing a side view of the same unit in FIG. 9B;

FIG. 10 is an exploded partially broken view in perspective of the lancet shown in FIG. 9;

FIG. 11 is a perspective partially broken view in smaller scale than FIG. 10 showing the lancet from the opposite end;

FIG. 12 is a diagrammatic sequential view showing the first step in usage by pulling off the cap;

FIG. 13 is a subsequent view showing the lancet placed in position on a finger for pricking the finger;

FIG. 14 is a view subsequent of that FIG. 13 showing compressing the lancet against the finger to activate the needle;

FIG. 15 is an exploded perspective view sequentially showing the seven elements which make up the adjustable disposable lancet;

FIG. 16 is a composite perspective view comparable to that shown in FIG. 15 but with the perspective taken from a different advantage point in showing the elements of FIG. 15 in greater detail;

FIG. 17 is a transverse sectional view of the lancet in its original condition as it arrives into the patient's possession, with the lancet in place and cocked and ready for use;

FIG. 18 shows the same lancet as in FIG. 17 but after the needle has been discharged and extended to its full penetration to a depth predetermined by the end support;

FIG. 19 is yet a further sequential view showing the lancet fully retracted after being discharged, as shown in FIG. 18, with the spring being in tension rather than compression as shown in FIG. 17 whereby withdrawing the lancet from its position outside the adjustable body; and FIG. 20 is a final view sequential to FIG. 19 showing the coil spring cutaway and illustrating how the tine, which is the longer length and angled at its remote end, prevents the reinsertion of the lancet into the cocked position for reuse, thereafter dictating disposal by the user.

Figure 21:
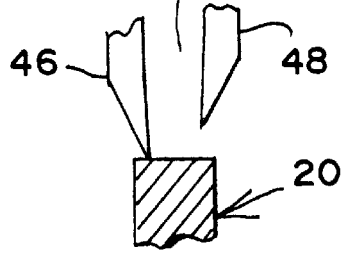

FIG. 21 is an enlarged diagrammatic view taken at 21—21 of FIG. 20.

DESCRIPTION OF A TYPICAL PRIOR ART LANCET

A typical prior art lancet is shown in FIG. 1. There will be seen lancet device 1 and an adjustable comfort tip 3. A cover needle cap is included in the comfort tip. The needle cap or disk 4 permits the lancet 6 to project the needle 5 after the cover has been removed, and activated by the trigger 8 to penetrate the epidermis.

More specifically, as shown in FIGS. 2 through 8, the first step is to twist off the lancing device the needle cap 4. Thereafter, a new lancet 6 is inserted into the lancet carrier. Subsequently, the needle cap is removed, revealing the needle ready for use. After which the lancing device needle cap is replaced on the lancing device.

At this point the comfort tip is rotated to adjust the same to the numerical indicia appearing opposite the arrow 7 thereon to determine the depth of the intended penetration. Once this adjustment has been completed, the needle cap 4 is separated from the barrel 2 thereby cocking the internal spring (not shown) in order to penetratingly drive the lancet needle into the finger. Finally, as shown in FIG. 8, the lancet device 1 is pressed against the finger, the trigger 8 activated, and the penetration of the finger is achieved. From here on out the patient squeezes a sufficient amount of blood on to a testing substrate, and the testing is completed in accordance with the prescribed protocol being followed.

DESCRIPTION OF THE PREFERRED EMBODIMENT

The general construction of the preferred embodiment appears in FIGS. 9A and 9B. There it will be seen that the adjustable disposable lancet 10 has a body portion 11 with a protective cap 12 having an internal needle protector 13 secured over the end. The selector tip 18 (FIG. 9B) is rotated until the depth positioning pointer 25 identifies the particular depth preselected. The selector tip 18 has a needle opening 19 which receives the needle 21 of the lancet 20.

The side view of FIG. 9B does not show the printed indicia or the pointer and it will be seen that the bottom end is uninterrupted.

As shown in FIG. 10, the contact pad 29 is on the end of the selector tip 18. The indicia is preselected by the depth positioning pointer 25 and the depth numbering 26 is shown on top of the body of the adjustable disposable lancet 10.

FIG. 11 is a reverse view of that shown in FIG. 10, differing only in that it does show the bottom to be uninterrupted.

In usage, the adjustable disposable lancet 10 is quite simplistic. As shown in FIGS. 12–13, the protective cap 12 is first removed from the adjustable disposable lancet 10. Thereafter, the selector tip 18 is rotated until the preselected notch is identified by the depth positioning pointer 25. The depth numbering 26 is employed as a guide, but it is actually the depth positioning pointer 25 which identifies the position notches 28 on the dial 51.

The specific structure is shown in exploded perspective in FIG. 15. Beginning at the lower left hand corner of FIG. 15 it will be seen that the protective cap 12 is positioned over the selector tip 18. In turn, the selector tip 18 fits within the body portion 11. The body portion 11, as shown, has an extended depth positioning pointer 25 which will be described hereinafter. The depth positioning pointer 25 extends from the body portion 11. The selector tip 18 receives the lancet 20 from which the needle 21 extends at one end. Spaced from the needle is the locking ring 23 which helps the securement of biasing means comprising the coil spring 15 at one of its ends 16 to the lancet 20. The lower spring end 16 of the coil spring 15 is positioned to coaxially engage the disabling tines 45. The latch means or latches 44 are opposed and engage the spring lock groove 22 defined by the locking ring 23 of the lancet 20. As to the disabling tines 45, it will be noted that there is a long tine tip 45 and a short tine tip 46. The longer of the tines tip 45, particularly as shown in FIG. 20, has its end cocked slightly inwardly, as will be described hereinafter. The space 38 between the tines 45, 45 comprises guide means for the lancet 20.

In greater detail, as to the specific structure which dictates the function and method of the subject adjustable disposable lancet, FIG. 16 shows the principal elements of FIG. 15 but in great detail. The details will be described proceeding from the selector tip 18 which appears in the upper right-hand corner of FIG. 16, downwardly through the depth positioning pointer 25, and thereafter to the lancet 20, and finally the mounting of the lancet 20 in the lancet holder 40. More specifically, it will be seen that the selector tip 18 has a plurality of selector knobs 56 underneath the contact pad 29. These selector knobs 56 are proportioned to click into the mating selector grooves 58 located in the depth positioning pointer 25 which is shown immediately beneath the selector tip 18 in FIG. 16. In addition, the action of a cam and follower comprising means interconnecting between the barrel and selector tip for adjusting the total length of the barrel, and selector tip includes the bayonet type helical recess 60 located in the lower barrel portion 61 of the selector tip 18 and the co-action between the cam follower pin 31 when it enters the slot of the bayonet type helix 60 moves the contact pad 29 upwardly or downwardly between the three positions. In so moving, the selector knobs 56 will selectively engage the recessed selector grooves 58 and in the process not only lockingly and removably securing the selector tip 18 internally of the depth positioning pointer 25 but also emitting an audible click each time the contact pad 29 is rotated between the three positions selected.

The specific details will be better understood now as we sequence through FIGS. 17, 18, 19 and 20. Beginning with FIG. 17, it shows the adjustable disposable lancet 10 as received by the user, with the protective cap 12 removed since the cap does figure into the action but rather serves to protect and enclose the unit for shipment, storage in the clinical facility, and sterility until actual use. As seen in FIG. 17, prior to usage the lancet needle 21 and lancet 20 are lockingly engaged by the disabling tines 45, 45 and more specifically the tine tips 46, 49 at the end portion of the disabling tines 45, 45. In accordance with the invention, it will be noted that one of the tines 45 is longer than the other tine 45. This tine length differential structure eliminates the possibility of re-inserting the lancet correctly after a single use, thereby comprising means for preventing recocking of the lancet 20 after it has been fired. Therefore, it will be seen that in FIG. 17 the contact pad 29, at the lower portion FIG. 18 shows the lancet in the fully extended position, at which time the coil spring 15 has gone from the compression mode as shown in FIG. 17 to a tension mode as shown in FIG. 18. It will be appreciated that this modal change of the coil spring 15 is virtually instantaneous and not observable. Nonetheless the coil spring 15 is so formed proportioned and of a metallic specification that permits the employment in a compression, as well as tension mode. At the time of the total penetration of the lancet needle 21, as shown in FIG. 18, it will be seen that the tines 45 and 45 in the lancet holder 40 are spread apart defining a tine slot 38, but the longer tine 45 has an offset in-portion which will be described hereinafter.

Turning now to FIG. 19, this is the configuration as the lancet 20 and its associated needle 21 is retracted during the after firing tension mode of the coil spring 15. As will be seen, the spring pulls on the groove 22 on the lancet 20 to yieldably urge the lancet 20 back into position in the tine slot 38 on the two disabling tines 45, 45.

As shown in FIG. 20, any return to a re-cocked position is frustrated by the long tine tip 45 and more particularly its end which is curved centrally, and therefore engages any portion of the I-beam like construction 36 of the lancet 20 which might try to bring the lancet base back between the tines 45, 45 in the tine slot 38 to the firing configuration, as shown in FIG. 17. In this fashion the lancet is prevented or frustrated from being repositioned over the tine members 45, 45, and reused. lockingly engaging the I-beam like construction 36 base of the lancet 20 in a pair of latches 44, and centrally positioning adjacent a pair of support tines extending upwardly from the base 41 of the lancet holder 40. Important to the invention is providing a latching means for the lancet in which the latching is conducted primarily by a pair of opposed locking and disabling tines. One of the tines 45 is longer than the other tine 45. This permits one of the longer tines 45 to be curved centrally so that upon the potential return of the lancet, that particular tine will engage the lancet much as shown FIG. 20 of the accompanying drawings. A dotted circle has been set on the position on FIG. 20, and FIG. 21 is a showing, in enlarged relatively diagrammatic form, how the longer of the tines 45 has its bent tip 49 and the same engages any lower portion of the lancet 20. The sequence of the method involves pre-selectively assembling all of the members at the factory site, and in such a fashion that the lancet 20 is cocked for usage, primarily as shown in FIG. 17. Thereafter the lancet contact pad 29 is rotatably adjusted to a predetermined position of the selector 50 which has selector knobs 56 which engage selector grooves 58 respectively on the selector tip 18 and inside of the lancet barrel-30 to thereby determine the extent to which the contact pad 29 extends from the main body portion of the disposable lancet. As set forth hereinabove, it is the utilization of the contact pad 29 by its spacial relationship from the balance of the unit which determines the extent of penetration of the lancet needle. The lancet needle 21 and the lancet 20 are always positioned in exactly the same location relative to the adjustable disposable lancet 10. More specifically, the body and all other elements are fixed. The depth numbering 26 indicates the extent to which the lancet body will be moved when it is fired, as shown in FIG. 18. No other element of the unit determines this position other than in their coordinated and cooperative relationship each to the other. The space 38 between the tines 45, 45 comprises guide means for the lancet 20, comprising means interconnecting between the barrel and selector tip for adjusting the total length of the barrel, and selector tip includes Also, in accordance with the invention, provision is made for a needle travel stop 32. The needle travel stop 32 is important in that it stops the penetration of the lancet 20 at a given point relative to the depth positioning pointer 25. As described earlier, the extent of penetration of the needle 20 is not a function of the positioning of the lancet. The lancet always positively engages the slide needle travel stop 32 and it is therefore the position of the selector tip 18 and it associated contact pad 29 that determine the penetration of the needle when the lancet is fired.

Turning now to FIG. 16, it will be seen that lancet barrel 30 houses the follower pin 31 and includes a needle travel stop 32, shown in phantom lines towards the upper portion of the barrel 30. Detents 34 are provided inside the barrel 30.

Continuing now, we skip to the lancet holder 40. As shown, the lancet holder 40 has a base portion 41. In addition, the lancet holder base 41 has basically an I-beam like construction 36 which permits it to be oriented into the lancet holder 40, as will be described hereinafter. The lancet holder 40 includes a pair of opposed latches identified as reference numeral 44. These latches 44 co-act with the locking ring 23 on the lancet 20 and co-act with the coil spring 15 in the compressed configuration when the lancet is set to fire.

The specific details will be better understood now as we sequence through FIGS. 17, 18, 19 and 20. Beginning with FIG. 17, it shows the adjustable disposable lancet 10 as received by the user, with the protective cap 12 removed since the cap does figure into the action but rather serves to protect and enclose the unit for shipment, storage in the clinical facility, and sterility until actual use. As seen in FIG. 17, prior to usage the lancet needle 21 and lancet 20 are lockingly engaged by the disabling tines 46 and more specifically the tine tips 48,49 at the end portion of the disabling tines 46. In accordance with the, invention, it will be noted that one of the tines 46 is longer than the other tine 45. This tine length differential structure thereby comprising means for preventing recocking of the lancet 20 after it has been fired. Therefore, it will be seen that in FIG. 17 the contact pad 29, at the lower portions thereof, is positioned with respect to the holder body by means of the position of the helix 55 and the helical engaging cam follows pin 31.

FIG. 18 shows the lancet in the fully extended position, at which time the coil spring 15 has gone from the compression mode as shown in FIG. 17 to a tension mode as shown in FIG. 18. It will be appreciated that this modal change of the coil spring 15 is virtually instantaneous and not observable. Nonetheless the coil spring 15 is so formed proportioned and of a metallic specification that permits the employment in a compression as well as tension mode. At the time of the total penetration of the, lancet needle 21, as shown in FIG. 18, it will beseem that the tines,45 and 46 in the lancet holder 40 are spread apart defining a tine slot 38, but the longer tine 45 has an offset in-portion which will be described hereinafter.

Turning now to FIG. 19, this is the configuration as the lancet 20 and its associated needle 21 is retracted during the after firing tension mode of the coil spring 15. As will be seen, the spring pulls on the groove 22 on the lancet 20 to yieldably urge the lancet 20 back into position in the tine slot 38 on the two disabling tines 46.

As shown in FIG. 20, any return to a re-cocked position is frustrated by the long tine tip 46 and more particularly its end which is curved centrally, and therefore engages any portion of the I-beam like construction 36 of the lancet 20 which might try to bring the lancet base back between the tines 45,46 in the tine slot 38 to the firing configuration, as shown in FIG. 17. In this fashion the lancet is prevented or frustrated from being repositioned over the tine members 45, and reused.

The Method

The method of the present invention involves the constraint of a lancet interiorly of a disposable lancet device. The sequence of the disposition of the lancet involves positioning a spring coaxially around the lancet base, and thereafter lockingly engaging the I-beam like construction 36 base of the lancet 20 in a pair of latches 44, and centrally positioning adjacent a pair of support tines extending upwardly from the base 41 of the lancet holder 40. Important to the invention is providing a latching means for the lancet in which the latching is conducted primarily by a pair of opposed locking and disabling tines. One of the tines 46 is longer than the other tine 45 This permits one of the longer tines 46 to be curved centrally so that upon the potential return of the lancet, that particular tine will engage the lancet much as shown FIG. 20 of the accompanying drawings. A dotted circle has been set on the position on FIG. 20, and FIG. 21 is a showing, in enlarged relatively diagrammatic form, how the longer of the tines 45 has its bent tip 49 and the same engages any lower portion of the lancet 20. The sequence of the method involves pre-selectively assembling all of the members at the factory site, and in such a fashion that the lancet 20 is cocked for usage, primarily as shown in FIG. 17. Thereafter the lancet contact pad 29 is rotatably adjusted to a predetermined position of the selector 50 which has selector knobs 56 which engage selector grooves 58 respectively on the selector tip 18 and inside of the lancet barrel 30 to thereby determine the extent to which the contact pad 29 extends from the main body portion of the disposable lancet. As set forth hereinabove, it is the utilization of the contact pad 29 by its spacial relationship from the balance of the unit which determines the extent of penetration of the lancet needle. The lancet needle 21 and the lancet 20 are always positioned in exactly the same location relative to the adjustable disposable lancet 10. More specifically, the body and all other elements are fixed. The depth numbering 26 indicates the extent to which the lancet body will be moved when it is fired, as shown in FIG. 18. No other element of the unit determines this position other than in their coordinated and cooperative relationship each to the other.

SUMMARY

In summary, what has been shown and described is an adjustable disposable lancet 10. Also shown and described is a method of utilization of an adjustable disposable lancet. While the method is dictated to a degree by the apparatus, the apparatus is also dictated by the method. In that respect, the method is specific to the utilization of the pad portion of a disposable lancet which contacts the body to determine the extent to which the lancet needle penetrates. Conversely, the structure of the body is such as to have a holding means for the lancet which has one end portion in interference relationship with the base of the lancet. Due to the interference relationship, while the lancet is properly oriented on top of the holding tines with the spring in compression prior to usage, once the lancet has been fired the holding tines will return to their original configuration with the longer of those tines 46 extending centrally 49 to thereby block any attempt to return the lancet to a cocked position.

It will be understood that various changes in the details, materials and arrangements of parts, or method which have been herein described and illustrated in order to explain the nature of the invention, may be made by those skilled in the art within the principle and scope of the invention as expressed in the appended claims.

PARTS LIST

| | | | | |
|---|---|---|---|---|
| 00 | | 34 | DETENT (FEMALE) | 68 |
| 01 | LANCET DEVICE | 35 | | 69 |
| 02 | BARREL | 36 | I-BEAM LIKE CONSTRUCTION | 70 |
| 03 | ADJUSTABLE COMFORT TIP | 37 | | 71 |
| 04 | NEEDLE CAP OR DISK | 38 | TINE SLOT | 72 |
| 05 | NEEDLE | 39 | | 73 |
| 06 | LANCET | 40 | LANCET HOLDER | 74 |
| 07 | ARROW | 41 | LANCET HOLDER BASE | 75 |
| 08 | TRIGGER | 42 | | 76 |
| 09 | | 43 | | 77 |
| 10 | ADJUSTABLE DISPOSABLE LANCET | 44 | LATCH | 78 |
| 11 | BODY | 45 | DISABLING TINES | 79 |
| 12 | PROTECTIVE CAP | 46 | LONG TINE TIP | 80 |
| 13 | NEEDLE PROTECTOR | 47 | | 81 |
| 14 | STATUS PIN | 48 | SHORT TINE TIP | 82 |
| 15 | COIL SPRING | 49 | CENTRALLY CURVED TIP | 83 |
| 16 | SPRING END | 50 | SELECTOR | 84 |
| 17 | | 51 | DIAL | 85 |
| 18 | SELECTOR TIP | 52 | | 86 |
| 19 | NEEDLE OPENING | 53 | | 87 |
| 20 | LANCET | 54 | | 88 |
| 21 | LANCET NEEDLE | 55 | HELIX SEGMENT (CAM) | 89 |
| 22 | SPRING LOCK GROOVE (20) | 56 | SELECTOR KNOBS | 90 |
| 23 | LOCKING RING | 57 | | 91 |
| 24 | | 58 | SELECTOR GROOVE | 92 |
| 25 | DEPTH POSITIONING POINTER | 59 | | 93 |
| 26 | DEPTH NUMBERING | 60 | BAYONET TYPE HELIX | 94 |
| 27 | | 61 | LOWER BARREL PORTION | 95 |
| 28 | POSITION NOTCH | 62 | | 96 |
| 29 | CONTACT PAD | 63 | | 97 |
| 30 | LANCET BARREL | 64 | | 98 |
| 31 | PIN (FOLLOWER) | 65 | | 99 |
| 32 | NEEDLE TRAVEL STOP | 66 | | 100 |
| 33 | | 67 | | 101 |

What is claimed is:

1. An adjustable disposable lancet device, comprising:
 a) an elongated body having a closed proximal end and an open distal end, said body having an internal chamber;
 b) a barrel slidably mounted in said chamber and protruding distally from said open distal end of said chamber, said barrel having an internal sub-chamber open proximally and distally;
 c) a lancet received within said chamber and sub-chamber and having a distally facing needle;
 d) said barrel having a distal opening to which a selector tip is attached; and
 e) means interconnecting between said barrel and selector tip for adjusting a total length of said barrel and selector tip to adjust depth of penetration of said needle past said selector tip, said interconnecting means comprising:
  i) a radially open part-circumferential ramp; and
  ii) a follower pin riding in said ramp;
  iii) whereby relative rotation of said selector tip with respect to said barrel in a first direction increases said total length, and relative rotation of said selector tip with respect to said barrel in a second direction reduces said total length.

2. The lancet device of claim 1, wherein said ramp is on said selector tip.

3. The lancet device of claim 2, wherein said follower pin is on said barrel.

4. The lancet device of claim 1, wherein said proximal end of said housing is closed by a lancet holder adapted to restrain said lancet in a cocked position thereof.

5. The lancet device of claim 4, wherein said lancet holder includes guide means for receiving a proximal end of said lancet to guide linear movements of said lancet.

6. The lancet device of claim 5, wherein said lancet holder includes means for preventing re-cocking of said lancet.

7. The lancet device of claim 6, wherein said re-cocking prevention means comprises a distal end of said guide means biased radially inwardly, whereby when said lancet is fired, said proximal end of said lancet is initially distal of said guide means, whereupon said biased distal end moves radially inwardly to prevent said proximal end of said lancet from re-entering said guide means.

8. The lancet device of claim 4, further including biasing means interposed between said lancet holder and said lancet for biasing said lancet toward said distal end of said body in said cocked position.

9. The lancet device of claim 8, wherein said barrel includes actuator means for releasing said lancet from said lancet holder to fire said lancet toward said distal end of said body.

10. The lancet device of claim 9, wherein said selector tip has an opening through which said needle protrudes when said lancet is fired.

11. The lancet device of claim 9, wherein said lancet holder includes latch means for latching said lancet in said cocked position.

12. The lancet device of claim 11, wherein said lancet includes a radially outwardly extending ridge, said latch means comprising diametrically opposed latches engaging said ridge in said cocked position.

13. The lancet device of claim 12, wherein reciprocation of said barrel proximally causes radially outward movement of said latches to release and fire said lancet.

14. A lancet device, comprising:
 a) an elongated body having a closed proximal end and an open distal end, said body having an internal chamber;
 b) a lancet disposed in said chamber and movable between a cocked position and a fired position;
 c) guide means on said proximal end of said body for receiving a proximal end of said lancet and guiding linear movement of said lancet within said body; and
 d) means associated with said proximal end of said body for preventing re-cocking of said lancet after said lancet has been fired.

15. The lancet device of claim 14, wherein said closed proximal end of said body is defined by a lancet holder, said guide means and said means for preventing re-cocking being carried on said lancet holder.

16. The lancet device of claim 15, wherein said means for preventing re-cocking comprises a portion of said guide means.

17. An adjustable disposable lancet device, comprising:
 a) an elongated body having an open proximal end closed by a lancet holder and an open distal end, said body having an internal chamber;
 b) a barrel slidably mounted in said chamber and protruding distally from said open distal end of said chamber, said barrel having an internal sub-chamber open proximally and distally;
 c) a lancet received within said chamber and sub-chamber and having a distally facing needle;
 d) said barrel having a distal opening to which a selector tip is attached;
 e) means interconnecting between said barrel and selector tip for adjusting a total length of said barrel and selector tip to adjust depth of penetration of said needle past said selector tip, said interconnecting means comprising:
  i) a radially open part-circumferential ramp in said selector tip; and
  ii) a follower pin on said barrel riding in said ramp;
  iii) whereby relative rotation of said selector tip with respect to said barrel in a first direction increases said total length, and relative rotation of said selector tip with respect to said barrel in a second direction reduces said total length; and
 f) said lancet holder being adapted to restrain said lancet in a cocked position thereof, and including guide means for receiving a proximal end of said lancet to guide linear movements of said lancet.

18. The lancet device of claim 17, wherein said lancet holder includes means for preventing re-cocking of said lancet.

19. The lancet device of claim 17, further including biasing means interposed between said lancet holder and said lancet for biasing said lancet toward said distal end of said body in said cocked position.

20. The lancet device of claim 17, wherein said barrel includes actuator means for releasing said lancet from said lancet holder to fire said lancet toward said distal end of said body.

* * * * *